US00PP24636P3

(12) United States Plant Patent
Brazelton et al.

(10) Patent No.: US PP24,636 P3
(45) Date of Patent: Jul. 15, 2014

(54) BLUEBERRY PLANT NAMED 'BLUE RIBBON'

(50) Latin Name: ***Vaccinium corymbosum* hybrid**
Varietal Denomination: Blue Ribbon

(75) Inventors: David M. Brazelton, Walterville, OR (US); Adam L. Wagner, Eugene, OR (US)

(73) Assignee: Fall Creek Farm and Nursery, Inc., Lowell, OR (US)

( * ) Notice: Subject to any disclaimer, the term of this patent is extended or adjusted under 35 U.S.C. 154(b) by 162 days.

(21) Appl. No.: 13/385,909

(22) Filed: Mar. 12, 2012

(65) Prior Publication Data

US 2013/0239265 P1 Sep. 12, 2013

(51) Int. Cl.
*A01H 5/00* (2006.01)

(52) U.S. Cl.
USPC ..... Plt./157

(58) Field of Classification Search
CPC ..... A01H 5/08
USPC ..... Plt./157
See application file for complete search history.

(56) References Cited

PUBLICATIONS

Pluto Upov Plant Variety Database 201303, retrieved on Oct. 3, 2013, retrieved from the Internet at <https://www3.wipo.int/pluto/user/en/index.jsp> 3 pp.*
Retrieved on Oct. 3, 2013, retrieved from the Internet at <http://tess2.uspto.gov/bin/showfield?f=doc&state=4803:2jjx7y.2.3> 2 pp.*

* cited by examiner

*Primary Examiner* — June Hwu
(74) *Attorney, Agent, or Firm* — Davis Wright Tremaine LLP; Dale C. Hunt; Wenhua Yu

(57) ABSTRACT

The new blueberry plant variety 'Blue Ribbon' is provided. 'Blue Ribbon' is a commercial variety intended for the hand harvest market. The variety produces a large berry with exceptional flavor and crunch. 'Blue Ribbon' is an early to mid-season variety, producing high yields of excellent quality fruit, with good post-harvest shelf life. The plant is vigorous with a semi-upright to spreading growth habit, and an estimated chilling requirement of 800-1000 hours.

3 Drawing Sheets

Latin name of the family, genus, and species:
Family—Ericaceae
Genus—*Vaccinium*
Species—*corymbosum* hybrid
Variety denomination: The new blueberry plant claimed is of the variety denominated 'Blue Ribbon'.

CROSS REFERENCE TO RELATED APPLICATIONS

None.

STATEMENT REGARDING FEDERALLY-SPONSORED RESEARCH AND DEVELOPEMNT

None.

BACKGROUND OF THE INVENTION

The present invention relates to the discovery of a new and distinct cultivar of northern highbush blueberry (*Vaccinium corymbosum* hybrid) and referred to as 'Blue Ribbon', also referred to as 'ZF05-009', as herein described and illustrated.

The new blueberry plant variety 'Blue Ribbon' was selected in Lowell, Oreg. in 2005. 'Blue Ribbon' is a commercial variety intended for the hand harvest market. The variety produces a large berry with exceptional flavor and crunch. 'Blue Ribbon' is an early to mid-season variety, ripening after Duke but before Draper (U.S. Plant Pat. No. 15,103), and producing high yields of excellent quality fruit with good post-harvest shelf life. The plant is vigorous with a semi-upright to spreading, growth habit, and an estimated chilling requirement of 800-1000 hours.

Pedigree and History: The new blueberry plant originated from a 2002 controlled cross pollination of 'G344' (pollen parent, unpatented) by 'Toro' (female parent, unpatented). The seedling was first selected from a high density field planting in the summer of 2005 and has been planted in replicated trials since 2008.

The new variety can be compared to commercial variety 'Duke' in that 'Blue Ribbon' ripens 1 to 2 weeks later, has higher yields, and firmer fruit.

The new variety can be compared to commercial variety 'Draper' in that 'Blue Ribbon' ripens 1 to 2 weeks earlier, has higher yields, and better flavor.

The new blueberry plant variety 'Blue Ribbon' has maintained its distinguishing characteristics throughout successive asexual propagations. The variety has been repeatedly asexually reproduced through softwood cuttings in Lowell, Oreg., and the clones are phenotypically identical to the original plant.

SUMMARY OF THE INVENTION

The new blueberry plant variety 'Blue Ribbon' has not been observed under all possible environmental conditions. The phenotype may vary somewhat with variations in environment and cultural practices such as temperature and light intensity without, however, any variance in genotype.

The following traits have been repeatedly observed in Lowell, Oreg., and are determined to be the unique characteristics of the new blueberry plant variety 'Blue Ribbon':

1. Large fruit with exceptional flavor and crunch.
2. Vigorous plant with long, arching branches and a semi-upright, to spreading growth habit
3. High yields

BRIEF DESCRIPTION OF THE DRAWINGS

The accompanying photographic illustration shows typical specimens in full color of the foliage and fruit of the new variety 'Blue Ribbon'. The colors are as nearly true as is reasonably possible in a color representation of this type.

BOTANICAL DESCRIPTION

Figure 1:
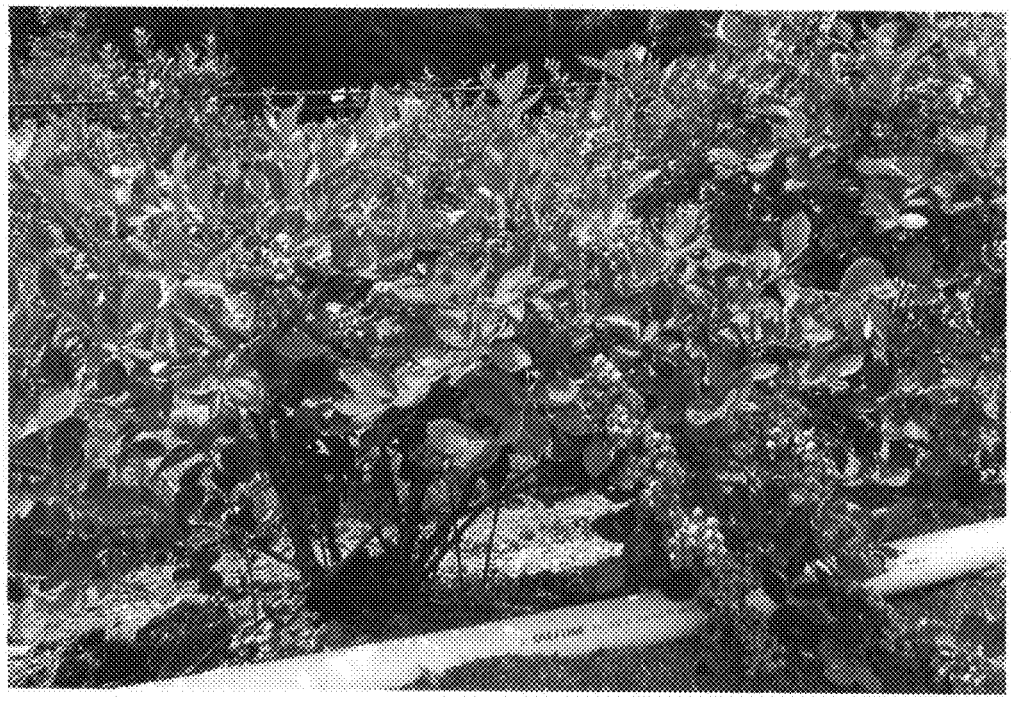
FIG. 1 is a photograph of the new variety 'Blue Ribbon', highlighting the plant's semi-upright to spreading growth habit and vigorous nature.
Figure 2:
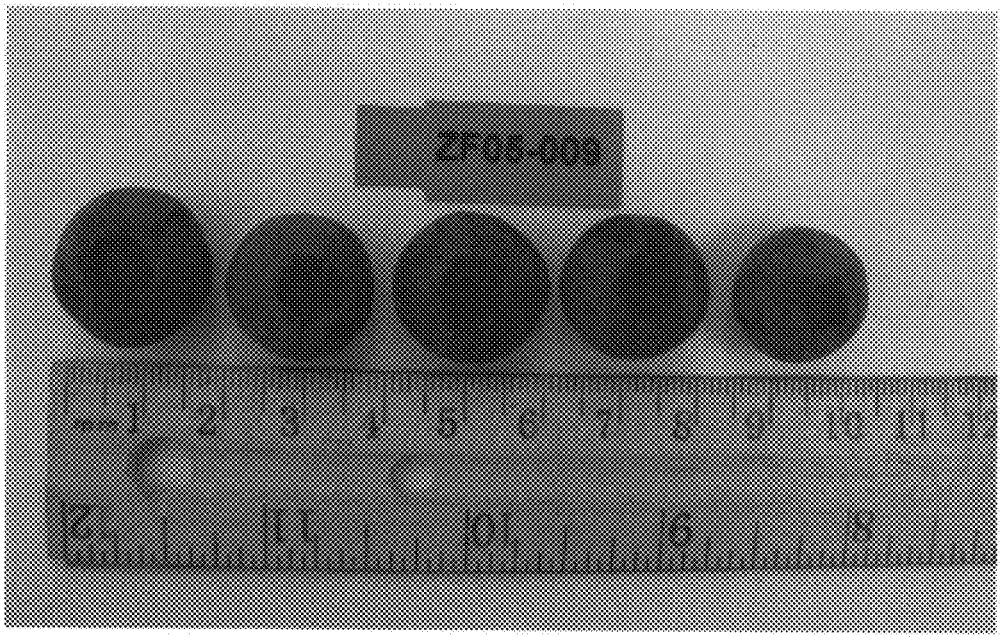
FIG. 2 is a photograph of the fruit of the new variety 'Blue Ribbon'.
Figure 3:
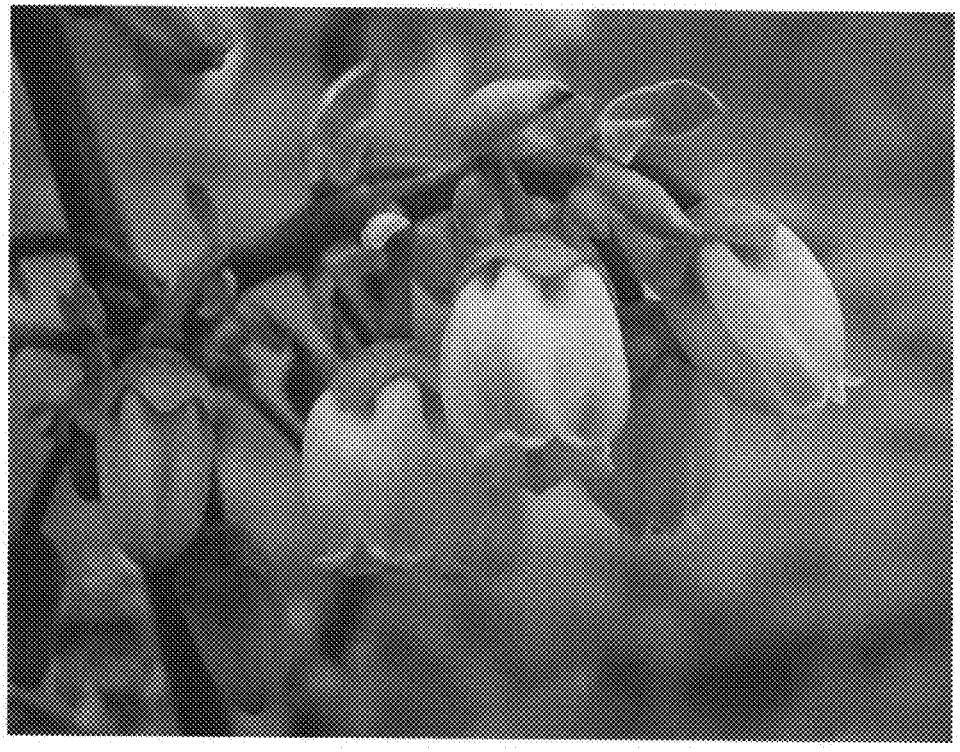
FIG. 3 is a photograph of the flowers of the new variety 'Blue Ribbon'.

The following detailed description sets forth the distinctive characteristics of 'Blue Ribbon'. The data which defines these characteristics was collected from asexual reproductions of the original selection. Dimensions, sizes, colors and other characteristics are approximations and averages set forth as accurately as possible. The plant history was taken on plants approximately three years of age, and the descriptions relate to plants grown in the field in Lowell, Oreg. Color designations are from "The Pantone Book of Color" (by Leatrice Eiseman and Lawrence Herbert; Harry N. Abrams, Inc., Publishers, New York, 1990). Where the Pantone color designations differ from the colors in the photographs, the Pantone colors are accurate.

Classification:

*a. Family.*—Ericaceae.
*b. Genus.*—*Vaccinium.*
*c. Species.*—*Corymbosum* hybrid.
*d. Common name.*—Northern Highbush.

Parentage:

*Female parent.*—'Toro' (unpatented).
*Male parent.*—'G344' (unpatented).

Market class: 'Blue Ribbon' is a commercial blueberry variety intended for the hand harvest market.

PLANT

Plant size: Medium.

*a. Height of plant.*—Average of 34 inches on 3 year old plants.
*b. Canopy diameter.*—Average of 41 inches on 3 year old plants.

Growth habit: Semi-upright to spreading with long, arching branches.
Plant vigor: Vigorous.
Twigginess: Low.
Evergreenness: Semi-deciduous in Lowell, Oreg.
Suckering: Low.
Chilling requirement: Approximately 800-1000 hours.
Cold hardiness: Approximately USDA zones 4-7.

Productivity: In Lowell, Oreg.:

*a. 2 year old plant.*—8.26 lbs per plant, compared to 4.22 lbs per plant on Duke plants of the same age.
*b. 3 year old plants.*—6.88 lbs per plant, compared to 4.14 lbs per plant on Duke plants of the same age.

Propagation: Easy to propagate from softwood cuttings.

Disease and pest resistance/susceptibility:

*a. Root rot* (*Phytophthora cinnamomi*).—Does not appear to be overly susceptible.
*b. Stem blight* (*Botryosphaeria spp*).—Undetermined.
*c. Phomopsis twig blight* (*Phomopsis vaccinii*).—Does not appear to be overly susceptible.
*d. Botryosphaeria stem canker* (*Botryosphaeria corticis*).—Undetermined.
*e. Bacterial cane canker* (*Pseudomonas syringae*).—Does not appear to be overly susceptible.
*f. Botrytis blight* (*Botrytis cinerea*).—Does not appear to be overly susceptible.
*g. Leaf spot* (*Septoria spp.*).—Does not appear to be overly susceptible.
*h. Leaf rust* (*Naohidemyces vaccinii*).—Does not appear to be overly susceptible.
*i. Bud mites* (*Acalatus vaccinii*).—Undetermined.

Disease survival: Good.

TRUNK AND BRANCHES

Texture:

*a. Surface texture new wood.*—Smooth.
*b. Surface texture 1 yr wood.*—Smooth.
*c. Surface texture 3 yr wood.*—Rough.

Color:

*a. Color new wood.*—Pantone color Oasis 16-0540 and Barn Red 18-1531.
*b. Color rough bark 1 yr.*—Pantone color Mineral Red 17-1537 and Oasis 16-0540.
*c. Color rough bark 3 yr.*—Pantone color Mineral Red 17-1537, Smoke Gray 14-1209, and Brush 16-1317.

FOLIAGE

Internode length: Average of 16.17 mm.

Leaf dimensions:

*a. Leaf length.*—Average of 58.6 mm.
*b. Leaf width.*—Average of 35.6 mm.

Leaf shape: Broadly elliptical.
Leaf margin: Entire.

Leaf color:

*a. Leaf color upper leaf surface.*—Pantone color Artichoke Green 18-0125.
*b. Leaf color lower leaf surface.*—Pantone color Epsom 17-0324.

Fall foliage color: 'Blue Ribbon' is highly evergreen and most leaves are retained without significant color change before frosts cause leaf drop. Most leaves darken from Artichoke Green 18-0125 to Pantone Thyme 19-039 without significant fall color change but some turn to Pantone Faded Rose 18-1629 before leaf drop.

Pubescence:

*a. Upper leaf surface.*—Absent.
*b. Lower leaf surface.*—Absent.
*c. Leaf margins.*—Absent.

Petiole:

*a. Length.*—Average of 4.38 mm.
*b. Color.*—Pantone color Sweet Pea 15-0531.
*c. Surface texture.*—Smooth.

FLOWERS

Flower arrangement: Alternate arrangement.
Fragrance: Sweet, faint.
Anther:
*a. Anther length.*—Average of 3.98 mm.
*b. Anther color.*—Pantone color Gold Earth 15-1234.
Immature flower color: Pantone color Holly Berry 17-1633 and Pastel Parchment 11-0603.
Pedicel:
*a. Pedicel length flower.*—Average of 4.48 mm.
*b. Pedicel color.*—Pantone color Spinach Green 16-0439, and Mauve Orchid 16-2111.
Peduncle:
*a. Peduncle length flower.*—Variable, average of 15.99 mm.
*b. Peduncle color.*—Pantone color Green Oasis 15-0538 and Mauve Orchid 16-2111.
Flower shape: Cylindrical to urceolate.
Pollen:
*a. Pollen staining.*—Approximately 85% viable, Staining with 2% acetocarmine dye.
*b. Pollen abundance.*—Medium pollen shed.
*c. Pollen color.*—Pantone color Cornsilk 13-0932.
Flower length: Average of 10.31 mm.
Corolla:
*a. Corolla length.*—Average of 8.21 mm.
*b. Corolla diameter.*—Average of 6.91 mm.
*c. Corolla color.*—Pantone color Snow White 11-0602.
*d. Corolla texture.*—Smooth.
*e. Corolla aperature.*—Average of 5.09 mm.
Style length: Average of 7.90 mm.
Calyx:
*a. Calyx diameter.*—Average of 5.54 mm.
*b. Calyx surface.*—Smooth.
*c. Calyx color.*—Pantone color Water cress 17-0220. Calyx Lobes — Spinach Green 16-0439 and Faded Rose 18-1629.
Pistil color: Pantone color Spinach Green 16-0439.
Flowering period: Flowers from the end of April through the end of May in Lowell, Oreg.
Flowering cluster: Moderately Loose.
Number of flowers: Average of 6 to 7 flowers per cluster.
Stigma location: Even with corolla to 0.08 mm below lip of corolla, on average.
Self-compatibility: Good — on average 86% of self-pollinated flowers reach maturity.
Precocity: Flower bud break occurs prior to vegetative bud break. Flowers persist during initial vegetative growth period.
Average inflorescence size: 30.78 mm.

FRUIT

Mean harvest date: July 21.
Mean date last pick: August 22.
Calyx:
*a. Calyx aperture.*—Average of 5.54 mm.
*b. Calyx lobes.*—5 lobes, not distinct.
*c. Calyx depth.*—Average of 1.09 mm.
Berry cluster: Moderately loose.
Berry pedicel:
*a. Length.*—Average of 8.99 mm.
*b. Surface texture.*—Smooth.
Berry peduncle:
*a. Length.*—Average of 24.70 mm.
*b. Surface texture.*—Smooth.
Berries per cluster: Average of 5 to 7.
Berry detachment: Moderately easy.
Berry weight: Average berry weight of 2.4 g, compared to Duke plants of the same age, which have an average berry weight of 2.4 g.
Berry height: Average of 13.04 mm.
Berry width: Average of 17.40 mm.
Berry shape: Oblate, spherical
Berry color:
*a. Immature berry color.*—Pantone color Green Olive 17-0535.
*b. Berry skin color on plant.*—Pantone color Blue Ice 17-3922.
*c. Berry skin color after harvest.*—Pantone color Velvet Morning 18-3927.
*d. Berry skin color after polishing.*—Pantone color Shale 19-3903.
Berry Wax: Medium wax/Moderately persistent.
Berry flesh color: Pantone color Celery Green 13-0532.
Pedicel scar: Small and dry, average of 2.54 mm inches in diameter.
Berry firmness: Very good. Average berry firmness measurement for 'Blue Ribbon' is 196 g/mm of deflection, compared to Duke plants harvested on the same day, which have an average of 148 g/mm of delfection as measured by a Firmtech fruit firmness machine.
Berry flavor: Sweet.
Berry texture: Smooth.

SEEDS

Seed color: Pantone color Marron 18-1415.
Seed length: Average of 1.65 mm.
Seed width : Average of 1 mm.
Seed weight: Average of 0.5 mg.
Seeds per berry: Average of 36 seeds per berry.

TABLE 1

DISTINGUISHING FEATURES FROM PARENTS

| Name of parent | Characteristic(s) in which the candidate variety differs from the parent | Describe the expression of the characteristic for the parent | Describe the expression of the characteristic for 'Blue Ribbon' |
|---|---|---|---|
| G344 | Growth habit | Semi-upright | spreading |
| G344 | Length of lateral shoots | Medium | Very long |
| Toro | Ripening time | Medium | early |
| Toro | Fruit firmness | Firm | soft |

The invention claimed is:

1. A new and distinct variety of blueberry plant named 'Blue Ribbon', substantially as illustrated and described herein.

* * * * *